United States Patent [19]

Barron et al.

[11] 4,231,839

[45] Nov. 4, 1980

[54] AFTER-TREATMENT PROCESSES AND APPARATUS, ESPECIALLY FOR UREA AND AMMONIUM NITRATE PLANTS

[75] Inventors: John W. Barron, Rockaway, N.J.; William H. Van Moorsel, Medicine Hat, Canada

[73] Assignee: CF Industries, Inc., Chicago, Ill.

[21] Appl. No.: 7,748

[22] Filed: Jan. 30, 1979

[51] Int. Cl.$^2$ .......................................... C07C 126/00
[52] U.S. Cl. ................................ 159/47 UA; 159/45; 159/17 R; 423/396; 564/65
[58] Field of Search ........... 159/45, 47 UA, 17, 28 A, 159/288; 423/416, 396; 260/555 A, 555 C

[56] References Cited

U.S. PATENT DOCUMENTS

| | | | |
|---|---|---|---|
| 3,255,246 | 6/1966 | Singer, Jr. | 260/555 A |
| 3,371,115 | 2/1968 | Cook et al. | 260/555 A |
| 3,585,237 | 6/1971 | Terrana et al. | 260/555 C |
| 3,723,430 | 3/1973 | Kokubo | 260/555 A |
| 4,087,513 | 5/1978 | Schell | 260/555 A |

*Primary Examiner*—Norman Yudkoff
*Attorney, Agent, or Firm*—Marvin A. Naigur; John E. Wilson; John J. Herguth, Jr.

[57] ABSTRACT

Disclosed are after-treatment processes and apparatus for synthesis plants, particularly urea and ammonium nitrate plants, but applicable also to various other plants in which the synthesis reaction does not go to substantial completion. In such plants product is fed to an evaporator for concentration and then to a solidification stage. The vaporous overhead stream from the evaporator contains entrained synthesis product, one or more unreacted starting materials, and solvent (usually $H_2O$). It is condensed, and the condensate is brought into mass and heat exchange relationship with the vaporous overhead stream from the evaporator substantially without material transfer of solvent to the condensate stream. The condensate stream is thereby enriched in synthesis product, heat is added to it, and unreacted starting material is desorbed from it. The product-enriched condensate is delivered to the solidification stage for processing there. Production capacity is increased and plant effluent is decreased or eliminated.

16 Claims, 2 Drawing Figures

AFTER-TREATMENT PROCESSES AND APPARATUS, ESPECIALLY FOR UREA AND AMMONIUM NITRATE PLANTS

BACKGROUND OF THE INVENTION

Urea and ammonium nitrate plants are two commercially important examples of synthesis plants of the kind in which the synthesis reaction reaches an equilibrium rather than going to completion, in which the product is relatively less volatile than the starting materials, and in which the raw product is processed though evaporator and solidification stages to produce a final product. The objects of these conventional after-treatment steps are to produce a relatively high purity product, recover solvent and unreacted starting materials, and reduce pollution in effluent streams.

In urea plants the vaporous overhead stream from the evaporator stage or stages contains significant quantities of entrained urea which, unless removed, ends up in the condensate formed from the overhead stream. Its presence there is troublesome, because it must be hydrolyzed (converted to $NH_3$ and $CO_2$). The hydrolysis products are separated from the water in the condensate and sent, along with unreacted starting material separated from the condensate, back into the reactor for reconversion into urea. These steps are necessary in order to raise the condensate to sufficient purity for discharge as effluent, as well as for efficient use of materials.

Similarly, in ammonium nitrate plants, the vaporous overhead stream from the evaporator stage or srtages contains entrained ammonium nitrate, which must be removed from the condensate before it can be discharged.

In conventional urea plants, the level of entrained urea in the evaporator overhead streams is reduced through the use of centrifugal or impingement type vane separators or similarly acting devices, but these devices still leave an objectionably high urea concentration in the condensate. This increases both plant capital and operating costs, because of the large condensate treatment system which must be provided and operated. In addition, it introduces inefficiencies and decreases plant capacity, because the already formed urea in the condensate is hydrolyzed back into starting materials which are then resynthesized into urea again. A portion of the synthesis section capacity is thus dedicated to this looping of materials, and is unavailable for production of usable product.

SUMMARY OF THE INVENTION

In accordance with the present invention, urea, ammonium nitrate, and similar processes and plants are improved by after-treatment processes and apparatus in which the vaporous overhead stream from the product evaporator stage is separated into non-condensibles and a derivative condensate. The condensate is then brought into mass and heat transfer relationship with the vaporous overhead stream, following which it is fed to the solidification stage for processing there, along with concentrate from the evaporator. These steps are performed continuously.

The vaporous overhead stream from the product evaporator stage contains entrained relatively non-volatile product, one or more relatively volatile starting materials, and vaporized solvent, usually $H_2O$. In the case of a urea process, it contains entrained urea, $NH_3$, $CO_2$ and $H_2O$. In the case of an ammonium nitrate process, it contains entrained ammonium nitrate, $NH_3$ and $H_2O$.

The condensate derived from the vaporous overhead stream contains relatively non-volatile product and one or more relatively volatile starting materials. In the case of a urea process, it contains urea, $CO_2$ and $NH_3$. In the case of an ammonium nitrate process, it contains ammonium nitrate and $NH_3$.

The conditions under which the overhead and condensate streams are brought into mass and heat transfer relationship are such that substantially no material amount of solvent is transferred from the overhead stream to the condensate stream.

In the mass and heat transfer step, three transfer reactions are accomplished:

(i) the concentration of entrained product (e.g. urea or ammonium nitrate) in the evaporator overhead stream is reduced, and the concentration of product in the condensate stream is correspondingly increased;

(ii) the temperature of the overhead stream is reduced (but not to the point that material amounts of solvent are condensed out of it) and heat is added to the condensate stream; and (iii) starting material (e.g. $NH_3$ and $CO_2$ in a urea process and $NH_3$ in an ammonium nitrate process) is desorbed from the condensate stream into the overhead stream, utilizing the heat added to the condensate from the overhead stream to drive this reaction.

Thus, the vaporous overhead stream is relatively leaner in product and richer in starting material than it would be in the absence of practice of the invention. This has several consequences which are advantageous compared to prior practice. It means that the derivative condensate, when initially formed, is also relatively leaner in product.

To the extent that such condensate is not cycled through the mass and heat transfer step involved in this invention, its leanness in product means that less product need be reconverted to starting material and stripped from the condensate, or otherwise removed from the condensate, in the condensate treatment stage of the overall process. In addition, diversion of part of the condensate away from the condensate treatment section and to the steps involved in this invention results in a reduction in the volume of condensate to be handled in the condensate treatment section. The need for less condensate treatment capacity leads to both equipment and operating economies in that stage of the process. Steam consumption in the condensate treatment stage is reduced.

Furthermore, in processes where product in the condensate is reconverted to starting material in the condensate treatment stage, and the starting material so produced is recycled back to the synthesis stage (as in conventional urea plants), the reduction of product level in the condensate accomplished by the present invention means that less of the synthesis section capacity must be devoted to producing product which is ultimately broken down and recycled. The production capacity thus freed from this duty may be utilized to produce salable product, and this is an extremely important advantage gained by the invention. Production capacity increases of five percent or more are thus made possible.

Finally, it should be noted that the reduction in product level in condensate fed to the condensate treatment stage materially simplifies the problem of treating the condensate, to the extent that conventional condensate treatment methods produce an output stream of sufficient quality that it may be used as make-up boiler feed water. Thus, treated condensate as a plant effluent stream may be eliminated altogether if desired.

As was pointed out above, the condensate stream, following the mass and heat transfer step, is relatively rich in product and relatively lean in starting materials. It thus forms a suitable feedstock for the solidification stage of the overall process and, in accordance with the invention, it is fed to the solidification stage for processing there along with the bottom stream from the evaporator stage or stages, the latter being the primary feed for the solidification stage.

The flow path of the condensate stream in the practice of the present invention should be sharply distinguished from commonly encountered reflux arrangements in which condensate from a column overhead stream is reintroduced into the top of a column, where it obviously is in mass and heat transfer contact with a vapor stream near the top of the column. In such reflux arrangements, however, the reintroduced condensate is not maintained as a separately identifiable stream; rather its constituents become merged, according to their properties, with the top, bottom, and side streams (if any) of the column. In the present invention, by contrast, the condensate stream is maintained as a separate stream before, during, and after the mass and heat transfer reaction. The product which is disentrained from the evaporator overhead stream into the condensate stream has no opportunity to be re-entrained back into the overhead stream, because the enriched condensate stream is continuously withdrawn and fed to the solidification stage after the mass and heat transfer step.

In some plants, particularly urea plants, the evaporator stage is subdivided into two stages through which the synthesis stage output is fed successively before it is passed to the solidification stage. In a plant so arranged, it is preferred that the condensate stream used in the mass and heat transfer reaction of the invention be formed of two components: (i) condensate from the first condenser for the second stage evaporator overhead, which is very high in product content, and (ii) condensate from the condensate collection system, which itself is a stream having several sources. It is preferred that these two components be combined and brought into heat and mass transfer relationship with the vaporous overhead stream from the first evaporator stage. In a urea plant this stream typically has a very high level of entrainment urea—as much as 95% on a weight basis.

As a matter of physical layout, it is preferred that the equipment be arranged so that the mass and heat transfer step of the invention is carried out in the separator section (upper portion) of the evaporator. Although various types of mass and heat transfer devices may be used, it is preferred that a bubble cap tray be employed because of its low pressure drop characteristics. It is also preferred that a baffle plate be mounted beneath the bubble cap tray for knocking down some of the entrained product, to reduce the load on the tray. Care must be taken in the design of the baffle plate so that plugging is minimized.

The evaporator overhead stream fed to the mass and heat transfer step of the invention is initially superheated, about 260° F. in the case of a urea plant. In its passage through the tray or other transfer device, it loses about 100° of temperature, but it is preferred that relatively little condensation of solvent be permitted in order to prevent a maldistribution or imbalance of solvent in the plant considered as a whole. The sensible heat provided by the temperature drop in the overhead stream is the driving force for desorbing starting material from the condensate.

As was mentioned above, the finally treated condensate from the condensate treatment section is of good enough quality to serve as make-up boiler feed water. It is also good enough quality for use in the pollution control process for fertilizer plants disclosed and claimed in U.S. Pat. No. 3,985,523.

From the foregoing it can be seen that a primary object of the present invention is the provision of an after-treatment process and apparatus for urea, ammonium nitrate, and similar plants which significantly increases production capacity without corresponding increases in capital and operating expense.

Another object of the invention is the provision of an after-treatment process and apparatus for such plants producing finally treated condensate usable internally in the plant, thereby eliminating condensate as an effluent stream.

A further object of the invention is to provide an after-treatment process and apparatus which reduces the quantity of condensate which must be handled as compared with a conventional plant.

Still another object of the invention is to provide an after-treatment process and apparatus which reduces the quantity of stream required for treating condensate, as compared with a conventional plant.

A related object is to reduce the quantity of product which must be reconverted to starting material in the course of condensate treatment, as compared with a conventional plant.

The manner in which these objects and purposes, together with other objects and purposes, are achieved in accordance with the invention may best be understood by a consideration of the detailed description which follows, together with the accompanying drawings.

DESCRIPTION OF THE PREFERRED EMBODIMENTS

Figure 1:
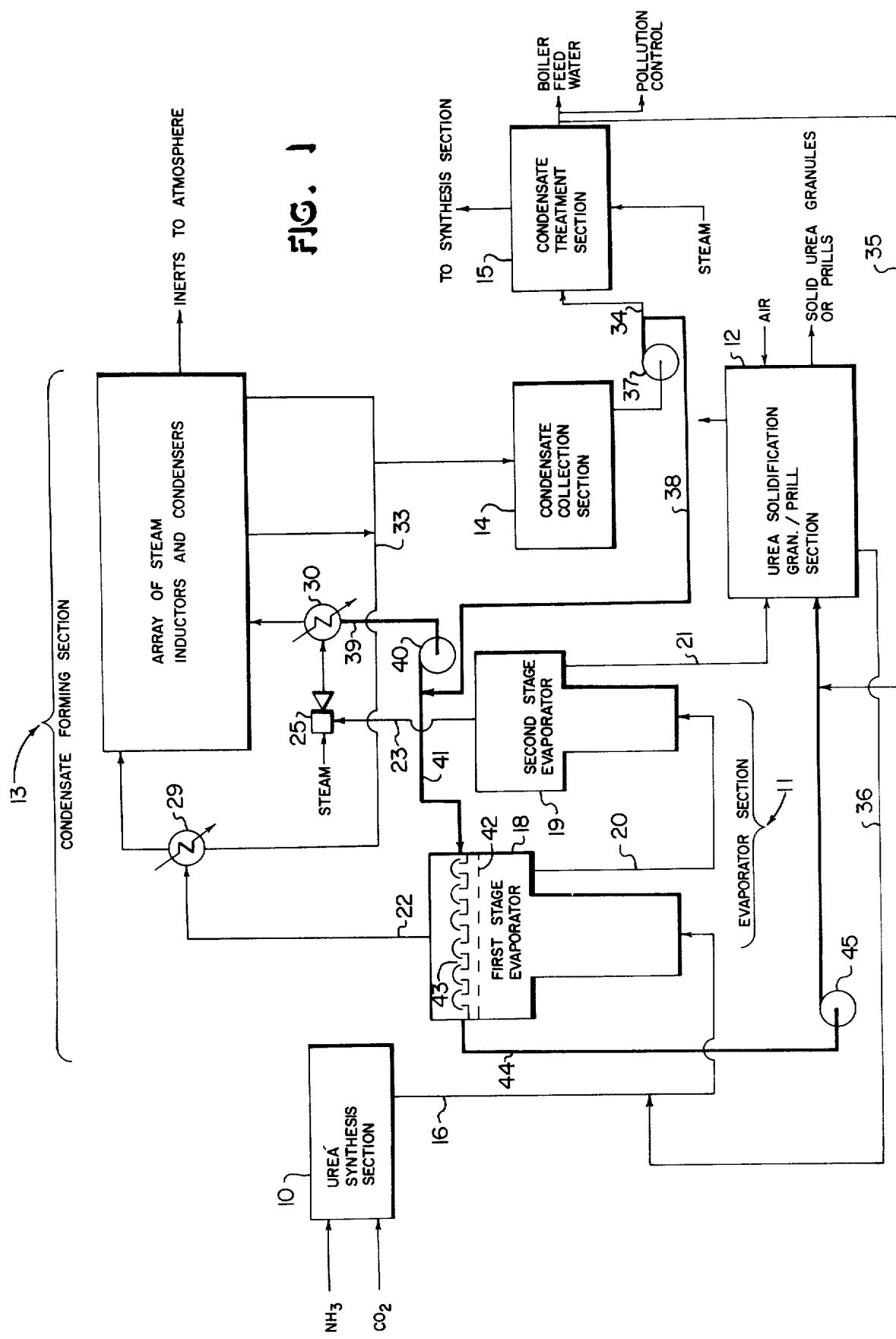
FIG. 1 is a schematic representation of a urea process and apparatus incorporating the present invention.

In FIG. 1, the process and apparatus of the present invention are shown as applied to an otherwise conventional urea process and plant.

The primary components of the urea plant are the urea synthesis section or stage 10; the evaporator section 11; the urea solidification section 12; the condensate forming section 13; the condensate collection section 14; and the condensate treatment section 15. A urea plant, of course, involves other equipment and sections than those shown, but the parts illustrated are those which are of interest for gaining an understanding of the present invention.

In the urea synthesis section 10, ammonia and carbon dioxide are reacted to form urea. The reaction does not go to completion; an equilibrium is reached, so that the product stream leaving the synthesis section 10 through line 16 contains unreacted starting material ($NH_3$ and $CO_2$) as well as urea and solvent ($H_2O$).

The product stream is delivered through line 16 to the evaporator section 11. In the plant shown in FIG. 1, the evaporator section 11 includes two evaporator stages 18 and 19, through which the product stream is fed sequentially by means of lines 16, 20 and 21. The urea becomes progressively more concentrated as it progresses through the evaporator section 11, as $NH_3$, $CO_2$, and $H_2O$ are stripped from it.

The concentrated urea is delivered through line 21 from the evaporator section 11 to the urea solidification section 12, where it is converted to a solid by either the prilling method or the granulating method, both of which are known. A recycle line 36 provides for returning urea to the first evaporator stage 18 if necessary.

Both evaporator stage 18 and evaporator stage 19 have overhead streams which pass through lines 22, 23 respectively into condensate forming section 13.

As can be seen from FIG. 1, the condensate forming section 13 is an array of steam inductors, one of which is 25, and an array of condensers, some of which are 29 and 30, together with interconnecting piping organizing the equipment so that each input stream into the condensate forming section is subjected to at least two stages of condensation. The piping also includes condensate collecting line 33, which gathers condensate from various condensers and delivers it to the condensate collection section 14. The precise arrangement of the condensate forming section is not critical to the practice of the present invention.

Condensate is fed from the condensate collection section 14 to the condensate treatment section 15 through line 34. In the treatment section 15, steam is supplied to further strip $NH_3$ and $CO_2$ from the condensate, and to hydrolyze urea to $NH_3$ and $CO_2$. The $NH_3$ and $CO_2$ are recycled to the synthesis section 10. The treated condensate is used as boiler feed water; or as feed to a pollution control system such as that shown in U.S. Pat. No. 3,985,523; or is recycled through line 35 to the urea solidification section; or is split among two or more such uses. The disposition of treated condensate may be varied in accordance with plant conditions and needs.

The equipment of FIG. 1 as described thus far is conventional.

In accordance with the invention, pump 37 delivers at least part of the condensate in the condensate collection section into line 38. Similarly, pump 40 delivers the condensate formed in condenser 30 (the second stage evaporator first stage condenser) through line 39. Both of these streams contain urea, $NH_3$ and $CO_2$. Lines 38 and 39 are joined into line 41, which delivers the combined streams to the upper portion of first stage evaporator 18.

In the upper portion of separator section of first stage evaporator 18 there is mounted a baffle plate 42, which intercepts the vaporous overhead stream passing upwardly through the evaporator. The baffle plate 42 serves to knock down or disentrain a portion of the urea in the overhead stream. It should be of fairly open configuration so it will not be susceptible to plugging.

Mounted above baffle plate 42 is bubble tray 43, also in position to intercept the vaporous overhead stream passing upwardly through the evaporator. The particular configuration of the bubble cap tray is not critical, but it should be constructed and arranged to impose only a slight pressure drop on the upflowing gas stream.

Line 41 delivers the combined condensate onto bubble tray 43. It flows across the tray and engages in mass and heat transfer with the vaporous overhead stream passing upwardly through the bubble caps, in the manner and with the effects described above.

Condensate, enriched in urea and leaned out in $NH_3$ and $CO_2$ is drawn off tray 43 through line 44, while the overhead stream, depleted in urea and enriched in $NH_3$ and $CO_2$ leaves the evaporator 18 and enters the condensate forming section 13 through line 22.

Pump 45 in line 44 delivers the urea enriched condensate to the solidification section 12.

Figure 2:
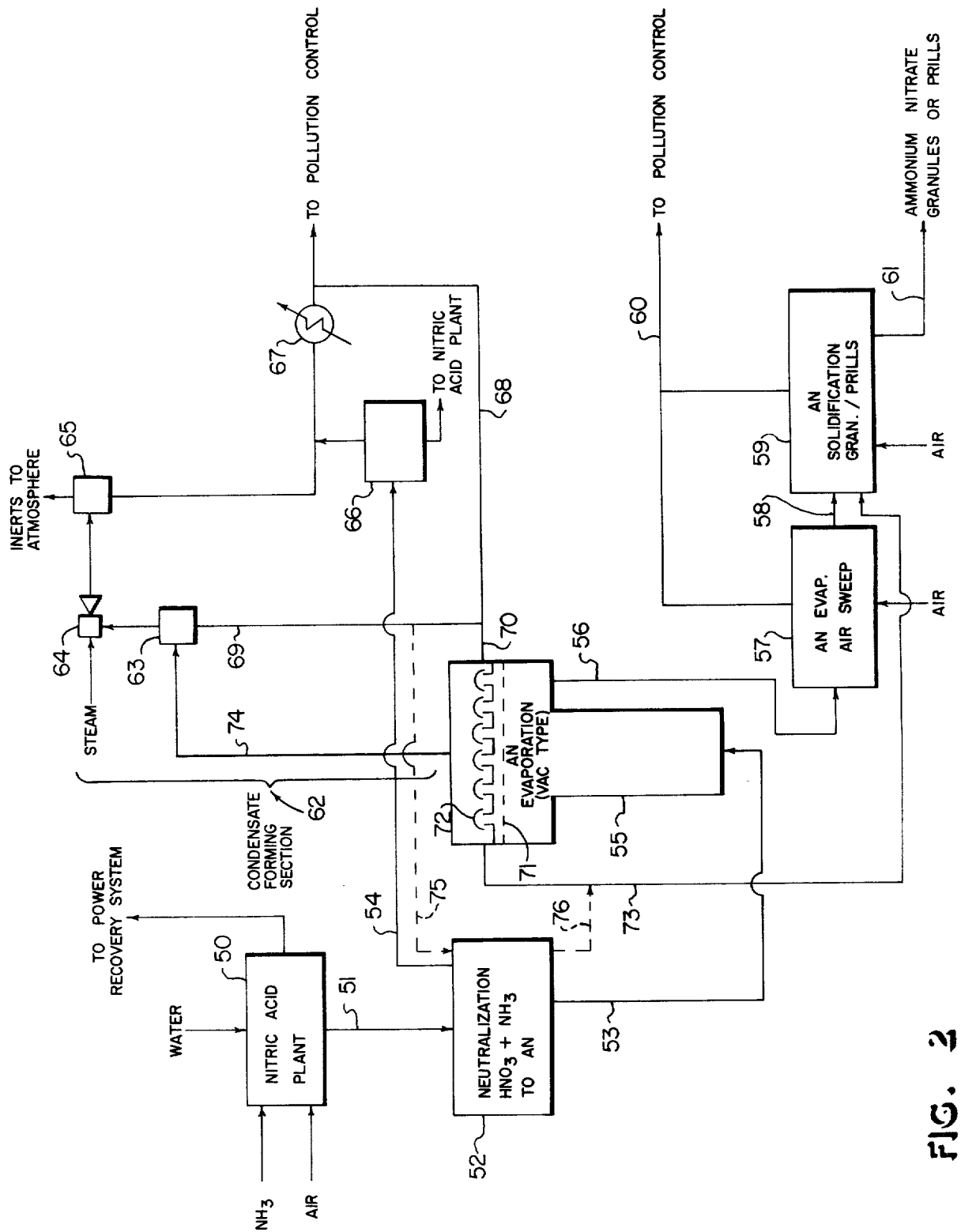
FIG. 2 is a schematic representation of an ammonium nitrate process and apparatus incorporating the present invention.

FIG. 2 illustrates the present invention as applied to an otherwise conventional ammonium nitrate process and plant.

The primary components of the ammonium nitrate plant shown in FIG. 2 are a nitric acid plant 50, a neutralization section 52, a first evaporator section 55, a second evaporator section 57, a solidification section 59, and a condensate forming section 62. An ammonium nitrate plant involves other equipment and sections, but those shown in the somewhat simplified diagram of FIG. 2 are those which are of interest for gaining an understanding of the present invention.

Ammonia, air, and water are reached in nitric acid plant 50 to form nitric acid, which is delivered through line 51 to neutralization section 52. There, the acid is reacted with ammonia to form ammonium nitrate. The product stream leaving the neutralization or synthesis section 52 through line 53 contains unreacted $NH_3$ as well as ammonium nitrate (designated "AN" in FIG. 2).

The product stream is fed to the first evaporator section 55 through line 53, and an overhead stream from the neutralization section is fed through line 54 to the condensate forming section 62. This overhead stream contains unreacted $NH_3$ and entrained ammonium nitrate.

In evaporator section 55, which is of the vacuum type, the ammonium nitrate is concentrated by the removal of $H_2O$ and unreacted $NH_3$. The overhead stream leaving evaporator section 55 through line 74 contains entrained ammonium nitrate as well as $NH_3$ and $H_2O$. Line 74 delivers the overhead stream to the condensate forming section.

The concentrated ammonium nitrate from evaporator section 55 is fed through line 56 to the second evaporator section 57, which is of the air-sweep type. There, it is further concentrated and fed through line 58 to solidification section 59, where the ammonium nitrate is formed into granules or prills, which leave through line 61. Both air-sweep evaporator 57 and solidification section 59 have overhead streams which are fed through line 60 to pollution control equipment.

The condensate forming section 62 includes a series of condensers 63, 65, 66 and 67, a steam inductor 64, and piping interconnecting them for separating condensibles out of the overhead streams from the neutralization section 52 and the vacuum evaporator 55. The detailed arrangement of the condensate forming section is not critical to the practice of the present invention.

The equipment of FIG. 2 as described thus far is conventional.

In accordance with the invention, condensate from the condensate forming section is fed through lines 68 and 69, which join in line 70, to first evaporator section 55. The condensate in these lines contains ammonium nitrate and NH$_3$.

In evaporator 55, baffle plate 71 is mounted in position to knock down entrained ammonium nitrate in the vaporous overhead stream from the evaporator. Above it is mounted bubble tray 72, which received condensate from line 70. The condensate flowing across tray 72 enters into the mass and heat transfer reactions discussed above with the vaporous overhead stream flowing upwardly through the bubble caps.

Condensate enriched in ammonium nitrate and stripped of NH$_3$ is drawn off tray 72 through line 73 and fed to ammonium nitrate solidification section 59.

In FIG. 2, a modification of the invention is indicated by dashed lines 75 and 76.

In accordance with the invention as modified, an additional bubble-cap tray is employed. It is located in the reactor separator forming part of the neutralization section 52. Condensate from the condensate forming section 62 is fed to the bubble-cap tray in the reactor separator in the neutralization section through line 75. The entrained ammonium nitrate in the vaporous overhead stream from the reactor separator 52 is knocked down on the bubble tray. The condensate generated by condenser 66 is thus made more suitable as water feeds to the nitric acid plant. Condensate enriched in ammonium nitrate is drawn off the bubble tray through line 76, combined with the stream in line 73, and fed to ammonium nitrate solidification section 59.

What is claimed is:

1. In a urea process of the kind in which product from a synthesis section is passed through at least one evaporator section for concentration prior to delivery to a solidification section, and in which said evaporator section has a vaporous overhead stream containing entrained urea, CO$_2$, NH$_3$, and H$_2$O, and further in which at least part of said evaporator section overhead stream is condensed to produce a derivative condensate stream containing dissolved entrained urea, CO$_2$, and NH$_3$; the improvement comprising:
   (a) bringing said vaporous overhead stream from said evaporator section into mass and heat transfer relationship with a stream consisting at least in part of said derivative condensate stream without materially transferring H$_2$O from said overhead stream to said condensate stream, to thereby:
      (i) reduced the entrained urea in said overhead stream and enrich the condensate in urea;
      (ii) reduce the temperature of said overhead stream and add heat to said condensate stream; and
      (iii) desorb CO$_2$ and NH$_3$ from said condensate stream into said overhead stream; and
   (b) delivering the urea-rich and CO$_2$, NH$_3$-lean condensate stream resulting from said mass and heat transfer step as a stream separate from concentrated product from said evaporator to said solidification section for processing there along with concentrated product from said evaporator.

2. A process in accordance with claim 1 in which said vaporous overhead stream from said evaporator and said derivative condensate stream are brought into mass and heat transfer relationship on a bubble-cap tray.

3. A process in accordance with claim 1 or 2 in which said vaporous overhead stream from said evaporator and said derivative condensate stream are brought into mass and heat transfer relationship in said evaporator section.

4. In a urea process of the kind in which product from a synthesis section is passed through first and second evaporator sections sequentially for concentration prior to delivery to a solidification section, and in which each of said evaporator sections has an overhead stream containing entrained urea, CO$_2$, NH$_3$, and H$_2$O, and further in which each of said overhead streams is separately at least partially condensed to produce derivative condensate streams containing dissolved entrained urea, CO$_2$ and NH$_3$; the improvement comprising;
   (a) combining at least some of said derivative condensate streams;
   (b) bringing the vaporous overhead stream from said first evaporator section into mass and heat transfer relationship with said combined derivative condensate stream without materially transferring H$_2$O from said overhead stream to said condensate stream, to thereby:
      (i) reduce the entrained urea in said overhead stream and enrich the condensate in urea;
      (ii) reduce the temperature of said overhead stream and add heat to said condensate stream; and
      (ii) desorb CO$_2$ and NH$_3$ from said condensate stream into said overhead stream; and
   (c) delivering the urea-rich and CO$_2$, NH$_3$-lean condensate stream resulting from said mass and heat transfer step as a stream separate from concentrated product from either of said evaporator sections to said solidification section for processing there along with concentrated product from said second evaporator section.

5. A process in accordance with claim 1 or 4 in which there is added to said derivative condensate stream additional condensate derived from an overhead stream from said synthesis section, prior to bringing said vaporous overhead evaporator section into mass and heat transfer relationship with said derivative condensate stream.

6. In an ammonium nitrate process of the kind in which product from a synthesis section is passed through at least one evaporator section prior to delivery to a solidification section, and in which said evaporator section has a vaporous overhead stream containing entrained ammonium nitrate, NH$_3$ and H$_2$O, and further in which at least part of said evaporator section overhead stream is condensed to produce a derivative condensate stream containing ammonium nitrate and NH$_3$; the improvement comprising:
   (a) bringing said vaporous overhead stream from said evaporator section into mass and heat transfer relationship with a stream consisting at least in part of said derivative condensate stream without materially transferring H$_2$O from said overhead stream to said condensate stream, to thereby:
      (i) reduce the entrained ammonium nitrate in said overhead stream and enrich the condensate in ammonium nitrate;
      (ii) reduce the temperature of said overhead stream and add heat to said condensate stream; and
      (iii) desorb NH$_3$ from said condensate stream into said overhead stream; and
   (b) delivering the ammonium nitrate-rich and NH$_3$-lean condensate stream resulting from said mass and heat transfer step as a stream separate from concentrated product from said evaporator to said solidification section for processing there along with concentrated product from said evaporator.

7. A process in accordance with claim 6 in which said vaporous overhead stream from said evaporator and said derivative condensate stream are brought into mass and heat transfer relationship on a bubble-cap tray.

8. A process in accordance with claim 6 in which said vaporous overhead stream from said evaporator and said derivative condensate stream are brought into mass and heat transfer relationship in said evaporator section.

9. In a process of the kind in which relatively nonvolatile product and residual unreacted relatively volatile starting material and solvent are passed through at least one evaporator section for concentration of the product and at least partial removal of starting material and solvent therefrom prior to delivery to a product solidification section, and in which said evaporator section has a vaporous overhead stream containing entrained product, starting material and solvent, and further in which at least part of said evaporator overhead stream is condensed to produce a derivative condensate stream containing dissolved entrained product and starting material; the improvement comprising:
  (a) bringing said vaporous overhead stream from said evaporator section into mass and heat transfer relationship with a stream consisting at least in part of said derivative condensate stream without materially transferring solvent from said stream to said concentrate stream, to thereby:
    (i) reduce the entrained product in said overhead stream and enrich the condensate in product;
    (ii) reduce the temperature of said overhead stream and add heat to said condensate stream; and
    (iii) desorb starting material from said condensate stream into said overhead stream; and
  (b) delivering the product-rich and starting material-lean condensate stream resulting from said mass and heat transfer step as a stream separate from concentrated product from said evaporator to said solidification section for processing there along with concentrated product from said evaporator.

10. A process in accordance with claim 9 in which said vaporous overhead stream from said evaporator and said derivative condensate stream are brought into mass and heat transfer relationship on a bubble-cap tray.

11. A process in accordance with claim 9 in which said vaporous overhead stream from said evaporator and said derivative condensate stream are brought into mass and heat transfer relationship in said evaporator section.

12. A process in accordance with claim 9 in which there is added to said derivative condensate stream additional condensate derived from an overhead stream from said synthesis section, prior to bringing said vaporous overhead evaporator section into mass and heat transfer relationship with said derivative condensate stream.

13. In a plant of the kind in which relatively nonvolatile product and residual unreacted relatively volatile starting material and solvent are passed through at least one evaporation section for concentration of the product and at least partial removal of starting material and solvent therefrom prior to delivery to a product solidification section, and in which said evaporator section has a vaporous overhead stream containing entrained product, starting material and solvent, and further in which at least part of said evaporator overhead stream is condensed to produce a derivative condensate stream containing dissolved entrained product and starting material; the improvement comprising:
  (a) means for bringing said vaporous overhead stream from said evaporator section into mass and heat transfer relationship with a stream consisting at least in part of said derivative condensate stream without materially transferring solvent from said stream to said concentrate stream, to thereby:
    (i) reduce the entrained product in said overhead stream and enrich the condensate in product;
    (ii) reduce the temperature of said overhead stream and add heat to said condensate stream; and
    (iii) desorb starting material from said condensate stream into said overhead stream; and
  (b) means for delivering the product-rich and starting material-lean condensate stream resulting from said mass and heat transfer step as a stream separate from concentrated product from said evaporator to said solidification section for processing there along with concentrated product from said evaporator.

14. A plant in accordance with claim 13 in which said means for bringing said vaporous overhead stream from said evaporator and said derivative condensate stream into mass and heat transfer relationship comprises a bubble-cap tray.

15. A plant in accordance with claim 13 or 14 in which said means for bringing said vaporous overhead stream from said evaporator and said derivative condensate stream into mass and heat transfer relationship are positioned in said evaporator section.

16. A plant in accordance with claim 13 and further comprising means for adding to said derivative condensate stream additional condensate derived from an overhead stream from said synthesis section, prior to bringing said vaporous overhead evaporator section into mass and heat transfer relationship with said derivative condensate stream.

* * * * *